(12) United States Patent
Yamamoto et al.

(10) Patent No.: US 10,960,331 B2
(45) Date of Patent: Mar. 30, 2021

(54) CELL-CAPTURING FILTER

(71) Applicant: Murata Manufacturing Co., Ltd., Nagaokakyo (JP)

(72) Inventors: Wataru Yamamoto, Nagaokakyo (JP); Masaru Banju, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 201 days.

(21) Appl. No.: 16/106,621

(22) Filed: Aug. 21, 2018

(65) Prior Publication Data

US 2018/0353881 A1 Dec. 13, 2018

Related U.S. Application Data

(63) Continuation of application No. PCT/JP2018/005513, filed on Feb. 16, 2018.

(30) Foreign Application Priority Data

Mar. 10, 2017 (JP) .............................. JP2017-046432

(51) Int. Cl.
*B01D 39/10* (2006.01)
*B01D 71/02* (2006.01)
(Continued)

(52) U.S. Cl.
CPC ................ *B01D 39/10* (2013.01); *C12M 1/12* (2013.01); *C12M 1/26* (2013.01); *C12M 33/14* (2013.01);
(Continued)

(58) Field of Classification Search
None
See application file for complete search history.

(56) References Cited

U.S. PATENT DOCUMENTS 4,894,343 A * 1/1990 Tanaka .................... C12M 23/20
210/498
8,273,253 B2 9/2012 Curran
(Continued)

FOREIGN PATENT DOCUMENTS

JP 2005148048 A 6/2005
JP 2010520446 A 6/2010
(Continued)

OTHER PUBLICATIONS

Written Opinion of the International Searching Authority issued for PCT/JP2018/005513, dated Apr. 10, 2018.
(Continued)

*Primary Examiner* — Krishnan S Menon
*Assistant Examiner* — Brad Gordon
(74) *Attorney, Agent, or Firm* — Arent Fox LLP (57) ABSTRACT

A cell-capturing filter that filters out cells includes a metallic porous film having a plurality of through holes that extend through a first main surface and a second main surface, which are opposite to each other. The metallic porous film includes a filtering portion including the plurality of through holes, and a frame portion disposed to surround an outer periphery of the filtering portion. In the filtering portion, a first film thickness of the metallic porous film at a center of the filtering portion is smaller than a second film thickness of the metallic porous film at a portion located closer to the frame portion than the center of the filtering portion.

17 Claims, 6 Drawing Sheets

(51) Int. Cl.
*C12M 1/00* (2006.01)
*C12M 1/26* (2006.01)
*G01N 1/40* (2006.01)
*G01N 1/34* (2006.01)
*C12M 1/12* (2006.01)
*B01D 63/08* (2006.01)
*B01D 69/12* (2006.01)
*B01D 69/02* (2006.01)
*B01D 61/18* (2006.01)

(52) U.S. Cl.
CPC ............ *C12M 47/02* (2013.01); *C12M 47/04* (2013.01); *G01N 1/34* (2013.01); *G01N 1/4077* (2013.01); *B01D 61/18* (2013.01); *B01D 63/087* (2013.01); *B01D 69/02* (2013.01); *B01D 69/12* (2013.01); *B01D 71/022* (2013.01); *B01D 2239/1291* (2013.01); *B01D 2315/08* (2013.01); *B01D 2325/04* (2013.01); *G01N 2001/4088* (2013.01)

(56) References Cited

U.S. PATENT DOCUMENTS

| | | | |
|---|---|---|---|
| 8,777,017 | B2 | 7/2014 | Curran |
| 10,022,659 | B2 | 7/2018 | Nakanishi et al. |
| 10,247,647 | B2 | 4/2019 | Kikuhara et al. |
| 2006/0252044 | A1* | 11/2006 | Okumura ......... G01N 33/54373 435/6.11 |
| 2009/0197009 | A1* | 8/2009 | Sugahara ............... B41J 2/1639 427/521 |
| 2010/0143879 | A1 | 6/2010 | Curran |
| 2012/0178097 | A1* | 7/2012 | Tai ..................... G01N 33/5011 435/7.1 |
| 2013/0098827 | A1 | 4/2013 | Curran |
| 2013/0264272 | A1* | 10/2013 | Jeon ....................... B01D 39/10 210/435 |
| 2016/0136552 | A1 | 5/2016 | Nakanishi et al. |
| 2016/0195458 | A1 | 7/2016 | Kikuhara et al. |
| 2017/0059460 | A1 | 3/2017 | Jeon et al. |
| 2017/0137769 | A1* | 5/2017 | Kikuhara ............... C12M 23/34 |
| 2017/0198248 | A1 | 7/2017 | Kinuta et al. |
| 2017/0216744 | A1 | 8/2017 | Kondo et al. |
| 2018/0312803 | A1 | 11/2018 | Banju et al. |

FOREIGN PATENT DOCUMENTS

| | | | |
|---|---|---|---|
| JP | 2013541958 | A | 11/2013 |
| JP | 6249124 | B1 | 12/2017 |
| WO | 2015012315 | A1 | 1/2015 |
| WO | 2015019889 | A1 | 2/2015 |
| WO | WO-2015145793 | A1 * | 10/2015 ........... G01N 33/491 |
| WO | 2016208362 | A1 | 12/2016 |
| WO | 2017022810 | A1 | 2/2017 |

OTHER PUBLICATIONS

Yusa et al., "Development of a New Rapid Isolation Device for Circulating Tumor Cells (CTCs) Using 3D Palladium Filter and its Application for Genetic Analysis," PLOS ONE, vol. 9(2), Feb. 2014, pp. 1-11.

International Search Report issued in PCT/JP2018/005513, dated Apr. 10, 2018.

* cited by examiner

CELL-CAPTURING FILTER

CROSS REFERENCE TO RELATED APPLICATIONS

The present application is a continuation of International application No. PCT/JP2018/005513, filed Feb. 16, 2018, which claims priority to Japanese Patent Application No. 2017-046432, filed Mar. 10, 2017, the entire contents of each of which are incorporated herein by reference.

FIELD OF THE INVENTION

The present invention relates to a cell-capturing filter that filters out cells.

BACKGROUND OF THE INVENTION

A filter including a metallic porous film is known to date as a cell-capturing filter that filters out cells in a fluid to capture the cells (see, for example, PTL 1).

Such an existing cell-capturing filter includes a metallic porous film including multiple through holes that extend through flat main surfaces opposite to each other. A fluid containing cells, which are to be filtered out, is fed from one main surface of the metallic porous film and caused to pass through the through holes so that the cells can be captured on the main surface.

PTL 1: Japanese Unexamined Patent Application Publication (Translation of PCT Application) No. 2010-520446

SUMMARY OF THE INVENTION

To analyze cells captured on one main surface of the metallic porous film of such an existing cell-capturing filter, the metallic porous film needs to be moved to an analyzer. However, scarcely any fluid such as a culture solution is left on the main surface of the metallic porous film. As such, the captured cells may be dried and damaged so that they are incapable of being analyzed.

The present invention aims to address the above existing problem and to provide a cell-capturing filter capable of improving the handleability of cells captured by a metallic porous film.

A cell-capturing filter according to an aspect of the present invention includes a metallic porous film having a plurality of through holes that extend through a first main surface and a second main surface, which are opposite to each other. The metallic porous film includes a filtering portion, in which the plurality of through holes are formed, and a frame portion, which is disposed to surround an outer periphery of the filtering portion. In the filtering portion, the metallic porous film at a center of the filtering portion has a film thickness smaller than a film thickness of the metallic porous film at a portion closer to the frame portion than the center of the filtering portion.

The present invention can provide a cell-capturing filter capable of improving the handleability of cells captured by a metallic porous film.

DETAILED DESCRIPTION OF THE PREFERRED EMBODIMENTS

A cell-capturing filter that filters out cells according to an aspect of the present invention includes a metallic porous film having a plurality of through holes that extend through a first main surface and a second main surface, which are opposite to each other. The metallic porous film includes a filtering portion, in which the plurality of through holes are formed, and a frame portion, which is disposed to surround an outer periphery of the filtering portion. In the filtering portion, the metallic porous film at a center of the filtering portion has a film thickness smaller than a film thickness of the metallic porous film at a portion closer to the frame portion than the center of the filtering portion.

In this structure, the metallic porous film at a center of the filtering portion has a film thickness smaller than a film thickness of the metallic porous film at a portion closer to the frame portion than the center of the filtering portion. Thus, at least one of the first main surface and the second main surface can partially have a concave surface in the filtering portion. When the surface having the concave surface is used to capture cells, the concave surface is more likely to allow a fluid puddle to be formed thereon with the effect of the surface tension of the fluid, so that the captured cells are prevented from being dried. This structure thus improves the handleability of cells captured by the metallic porous film.

In the filtering portion, the metallic porous film may have a film thickness increasing continuously or stepwise from the center of the filtering portion toward the frame portion.

In this structure, a smooth concave surface can be formed on the first main surface or the second main surface of the metallic porous film. The smooth concave surface thus formed is more likely to allow a fluid puddle to be formed thereon with the effect of the surface tension of a fluid exerted on the concave surface. Thus, the handleability of cells captured by the metallic porous film can be improved. The surface tension of a fluid can be controlled by changing, in accordance with the viscosity of the fluid, the surface state of the metallic porous film, the shape of the through holes, or the opening area.

The second main surface of the metallic porous film may be a flat surface, and the first main surface at the filtering portion may be a concave surface having a portion closer to the center of the filtering portion lowered and a portion closer to the frame portion raised.

To use a fluid puddle formed using the concave surface, cells may be captured on the first main surface having the concave surface. On the other hand, to facilitate removal of the fluid without allowing a fluid puddle to be formed, cells may be captured on the second main surface having a flat surface. By thus differently using the first main surface and the second main surface for different purposes, the handleability of the cell-capturing filter can be improved.

In a direction parallel to the second main surface of the metallic porous film, the frame portion has a width greater than a distance between adjacent through holes of the plurality of through holes in the filtering portion.

Making the width of the frame portion different from the distance between adjacent through holes enables varying the film thickness of the filtering portion through, for example, plating using a resist image. This structure can thus provide a cell-capturing filter that can improve the handleability of cells captured by the metallic porous film.

Embodiments of the present invention are described below with reference to the appended drawings. The drawings illustrate components in an exaggerated manner for ease of illustration.

FIRST EMBODIMENT

Entire Structure of Filter

Figure 1:
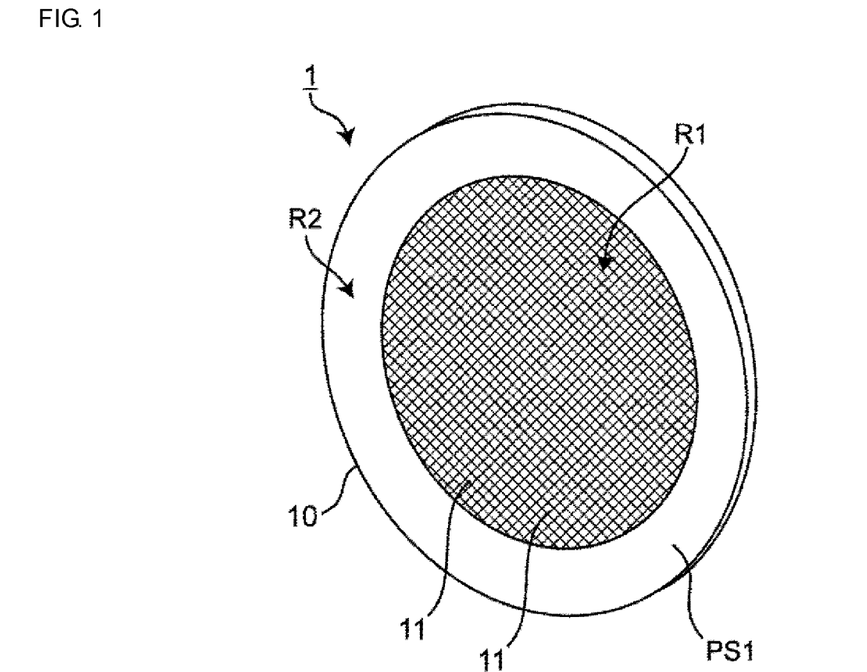
FIG. 1 is a schematic diagram of a structure of a filter according to an embodiment of the present invention.
Figure 2:
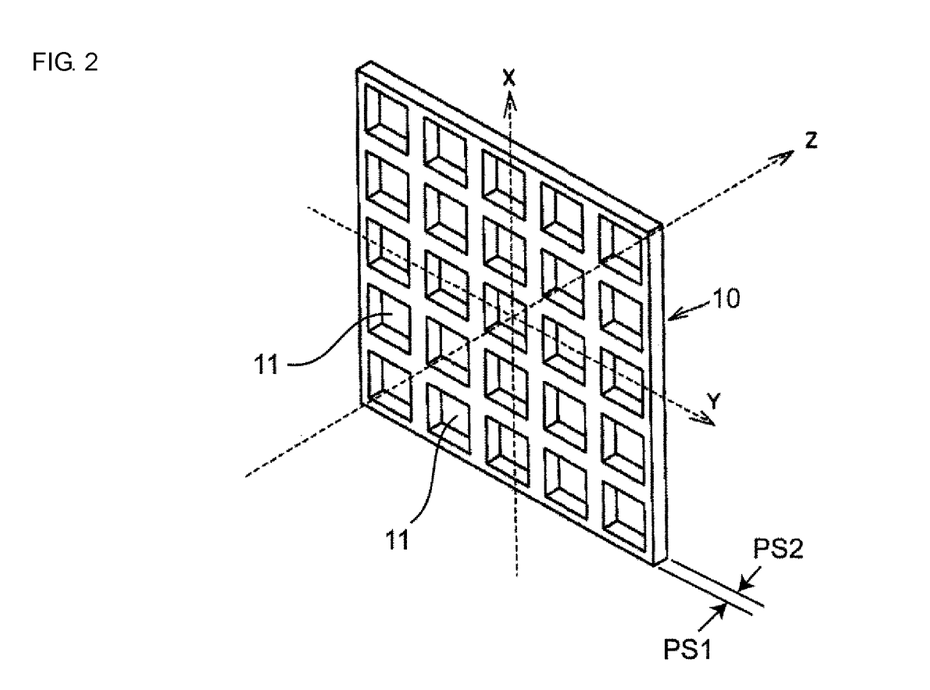
FIG. 2 is an enlarged view of a portion of a metallic porous film of the filter illustrated in FIG. 1.
Figure 3:
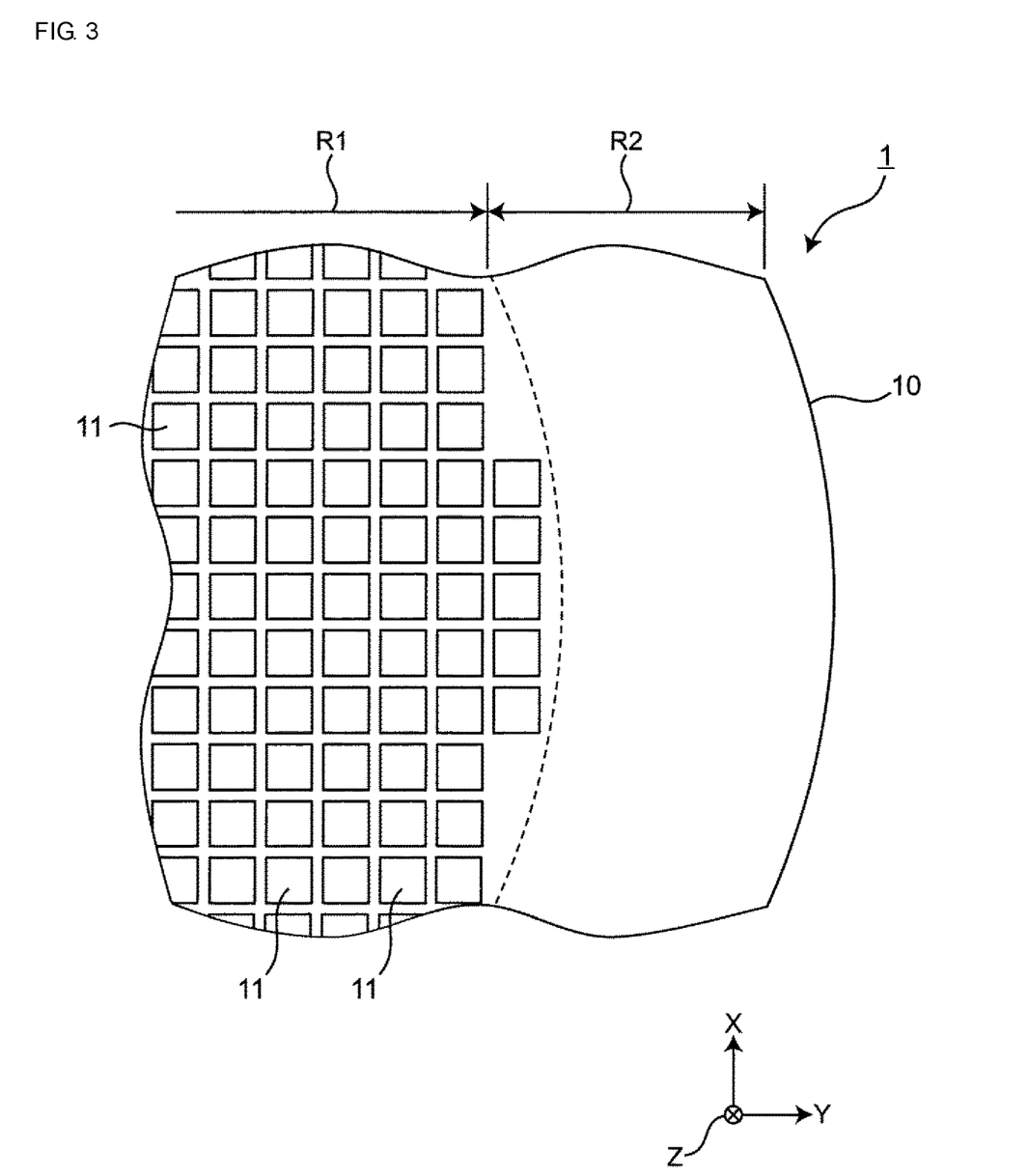
FIG. 3 is an enlarged view of a portion of the metallic porous film of the filter illustrated in FIG. 1.

FIG. 1 is a schematic diagram of a cell-capturing filter 1 (hereinafter referred to as a filter 1) according to a first embodiment of the present invention. FIG. 2 is an enlarged view of a portion of the filter 1. FIG. 3 is an enlarged plan view of a portion of the filter 1 near the periphery. X and Y directions in FIG. 2 are directions parallel to the surface of the filter 1 and orthogonal to each other. A Z direction is a thickness direction of the filter 1 and perpendicular to the X direction and the Y direction.

As illustrated in FIG. 1 and FIG. 3, the filter 1 includes a metallic porous film 10 including multiple through holes 11 that extend through in the thickness direction. The metallic porous film 10 includes a filtering portion R1, which is an area in which the multiple through holes 11 are formed, and a frame portion R2, which is an area surrounding the filtering portion R1. In the present first embodiment, the filtering portion R1 is a circular area. The frame portion R2 is an annular area, which is an area that holds the filtering portion R1 at the periphery. The frame portion R2 has no through hole 11. The filter 1 may include a member that clamps the frame portion R2 of the metallic porous film 10 to enhance the handleability of the filter 1. The present first embodiment describes, as an example, a case where the filtering portion R1 and the frame portion R2 are integrated. However, the filtering portion R1 and the frame portion R2 may be separate from each other and the frame portion R2 may hold the filtering portion R1. The shape of the filtering portion R1 is not limited to a circle and may be another shape such as a regular square, a rectangle, or an ellipse.

The metallic porous film 10 allows a fluid containing an object intended to be filtered out to pass through the through holes 11 to separate the object intended to be filtered out from the fluid. In the description, the "object intended to be filtered out" refers to an object that is to be filtered out by the metallic porous film 10. Examples of the object intended to be filtered out include biologically derived substances and PM2.5. Here, "biologically derived substances" refer to biologically derived substances such as cells (eukaryote), bacteria (true bacteria), and viruses. Examples of cells (eukaryote) include induced pluripotent stem cells (iPS cells), embryonic stem (ES) cells, stem cells, mesenchymal stem cells, mononuclear cells, single cells, cell masses, floating cells, adherent cells, nerve cells, white blood cells, regeneration medicine cells, self-cells, cancer cells, circulating cancer cells (CTC), HL-60 cells, HeLa cells, and fungi. Examples of bacteria (true bacteria) include colon bacilli and tubercle bacilli.

As illustrated in FIG. 1, the metallic porous film 10 is a circular metal mesh. As illustrated in FIG. 2, the metallic porous film 10 has a structure that includes a first main surface PS1 and a second main surface PS2, which are opposite to each other, and multiple through holes 11, which extend through both main surfaces. The multiple through holes 11 are arranged at regular intervals in the first main surface PS1 and the second main surface PS2 in the filtering portion R1 of the metallic porous film 10. The metallic porous film 10 contains, for example, nickel as a main component. The metallic porous film 10 may contain any metal as a main component, for example, gold, silver, copper, nickel, stainless steel, palladium, titanium, or an alloy of any of these. Particularly, from the view point of biocompatibility with biologically derived substances, gold, nickel, stainless steel, or titanium is preferable as the main component of the metallic porous film 10 to capture biologically derived substances.

As illustrated in FIGS. 2 and 3, the metallic porous film 10 has a plate-like structure (lattice structure) in which the multiple through holes 11 are arranged in a matrix at regular intervals. The multiple through holes 11 have a square shape when viewed from the first main surface PS1 of the metallic porous film 10, that is, viewed in the Z direction. The multiple through holes 11 are equidistantly arranged in two arrangement directions parallel to the sides of the squares, that is, in the X direction and the Y direction in FIG. 2. The shape of the through holes 11 is not limited to a regular square, and may be, for example, a rectangle, a circle, or an ellipse. The arrangement of the holes is not limited to the tetragonal lattice arrangement. For example, as long as being arranged in a quadrangle, the holes may be arranged in a rectangular arrangement in which the intervals in the two arrangement directions are not equal to each other, in a triangular lattice arrangement, or in a quasi-periodic arrangement.

The shape or size of the through holes 11 is appropriately designed in accordance with the size or shape of an object intended to be filtered out. In the present first embodiment, each through hole 11 is, for example, a regular square when viewed from the first main surface PS1 of the metallic porous film 10, that is, viewed in the Z direction, and is designed to have a length of greater than or equal to 0.1 µm to smaller than or equal to 50 µm and a width of greater than or equal to 0.1 µm to smaller than or equal to 50 µm. Each interval between the through holes 11 is, for example, greater than once the through hole 11 and smaller than or equal to ten times of the through hole 11, more preferably, smaller than or equal to three times of the through hole 11. Alternatively, each through hole 11 preferably has an aperture ratio of higher than or equal to 10%. In the direction parallel to the second main surface PS2 of the metallic porous film 10, the frame portion R2 has a width greater than a distance between the through holes 11 adjacent to each other in the filtering portion R1 (distance between the edges of the through holes 11).

Figures 4A, 4B:
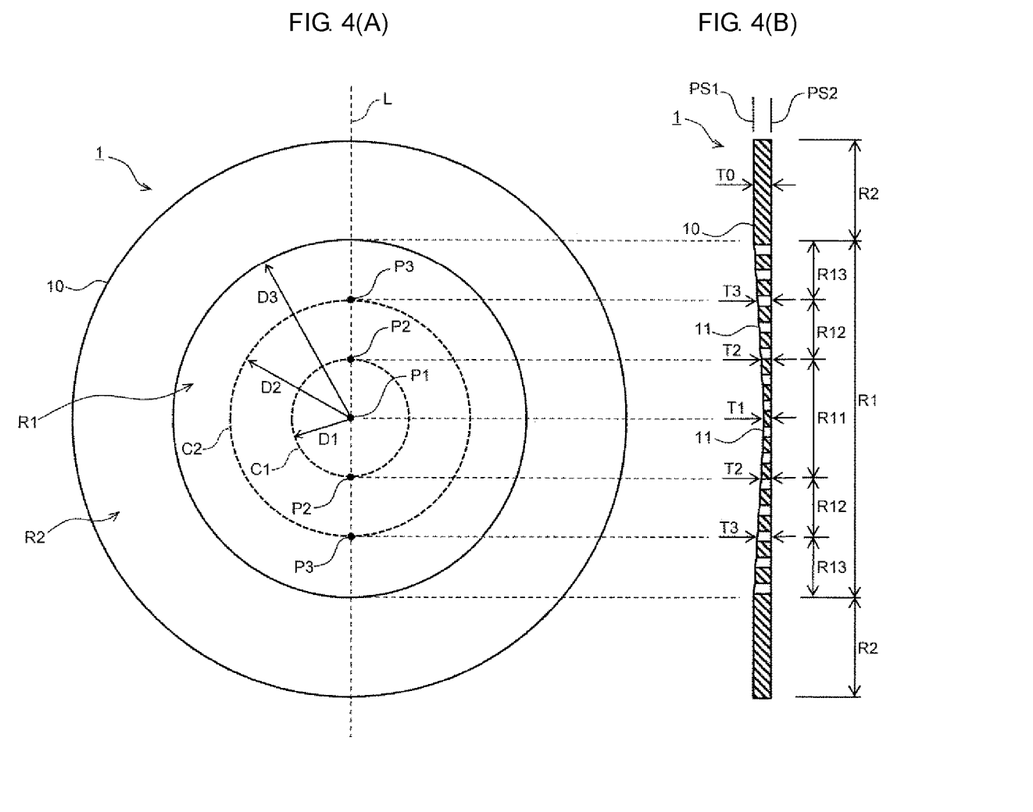
FIG. 4(A) is a schematic plan view of the structure of the metallic porous film of the filter illustrated in FIG. 1.
FIG. 4(B) is a schematic sectional view of the filter illustrated in FIG. 1.

FIGS. 4(A) and 4(B) are schematic diagrams of a structure of the filter 1 according to the present first embodiment. FIG. 4(A) is a schematic plan view of the filter 1, and FIG. 4(B) is a schematic sectional view of the filter 1.

As illustrated in FIG. 4(B), instead of having a uniform film thickness, the metallic porous film 10 of the filter 1 has its film thickness at a center portion smaller than that at the periphery. Specifically, in the filtering portion R1 of the metallic porous film 10, a center of the filtering portion R1 has a film thickness smaller than the film thickness of the metallic porous film 10 at a portion closer to the frame portion R2 than the center of the filtering portion R1.

As illustrated in FIG. 4(A), the entirety of the filtering portion R1 is a circular area having a radius D3 with respect to a center P1. In the filtering portion R1, imaginary circles C1 and C2 respectively having radii D1 and D2 with respect to the center P1 are drawn. Here, the radius D1 is one third of the radius D3, and the radius D2 is two thirds of the radius D3. In the filtering portion R1, the circular area encircled with the imaginary circle C1 is defined as a central area R11, an annular area interposed between the imaginary circle C1 and the imaginary circle C2 is defined as an intermediate area R12, and an annular area on the outer side of the imaginary circle C2 is defined as a peripheral area R13. When an imaginary straight line L passing the center P1 of the filtering portion R1 is drawn in a plan view of the filtering portion R1, the points of intersection (first position) between the imaginary straight line L and the imaginary circle C1 are denoted with P2, and the points of intersection (second position) between the imaginary straight line L and the imaginary circle C2 are denoted with P3.

FIG. 4(B) is a schematic sectional view of the imaginary straight line L in the metallic porous film 10 illustrated in FIG. 4(A). As illustrated in FIG. 4(B), the filtering portion R1 of the metallic porous film 10 has a film thickness in the central area R11, which is away from the frame portion R2, smaller than the film thickness in the peripheral area R13, which is closer to the frame portion R2 than the central area R11. In addition, in the filtering portion R1, the intermediate area R12 located between the central area R11 and the peripheral area R13 has a film thickness greater than the film thickness of the central area R11 and smaller than the film thickness of the peripheral area R13. Specifically, these film thicknesses satisfy the relationship of $T1<T2<T3$, where the film thickness at the center P1 is denoted with T1, the film thickness at the points of intersection P2 is denoted with T2, and the film thickness at the points of intersection P3 is denoted with T3. Specifically, in the filtering portion R1 of the metallic porous film 10, the film thickness is determined to increase radially (that is, toward the frame portion R2) from the center P1 of the filtering portion R1. The film thickness may increase continuously or stepwise.

As illustrated in FIG. 4(B), the second main surface PS2 of the metallic porous film 10 is a flat surface. The surface in the first main surface PS1 corresponding to the filtering portion R1 is a concave surface having a portion closer to the frame portion R2 higher than a portion closer to the center P1 of the filtering portion R1. The frame portion R2 of the metallic porous film 10 has a film thickness T0 that is approximately uniform. The film thickness T0 is greater than or equal to the film thickness T3 at the points of intersection P3 in the peripheral area R13.

The metallic porous film 10 according to the present first embodiment has, for example, a diameter of 8 mm (contour of the frame portion R2), a width of the frame portion R2 of 1 mm, and an interval between adjacent through holes 11 of greater than or equal to 1 µm to smaller than or equal to 500 µm. The filtering portion R1 has a diameter of 6 mm. In the filtering portion R1, the film thickness T3 at the points of intersection P3 closer to the frame portion R2 is 1.1 µm, and the film thickness T1 at the center P1 is 0.8 µm.

The description of the areas R11, R12, and R13 illustrated in FIGS. 4(A) and 4(B) is provided to describe an increase of the film thickness from the center P1 of the filtering portion R1 toward the frame portion R2. Thus, the structure is not limited the case where the radius D1 of the imaginary circle C1 is one third of the radius D3, and the radius D2 of the imaginary circle C2 is two thirds of the radius D3. For example, the description may be similarly provided using an imaginary circle in which the respective radii have the relationship of $D1<D2<D3$.

Method for Manufacturing Filter

Figure 5:
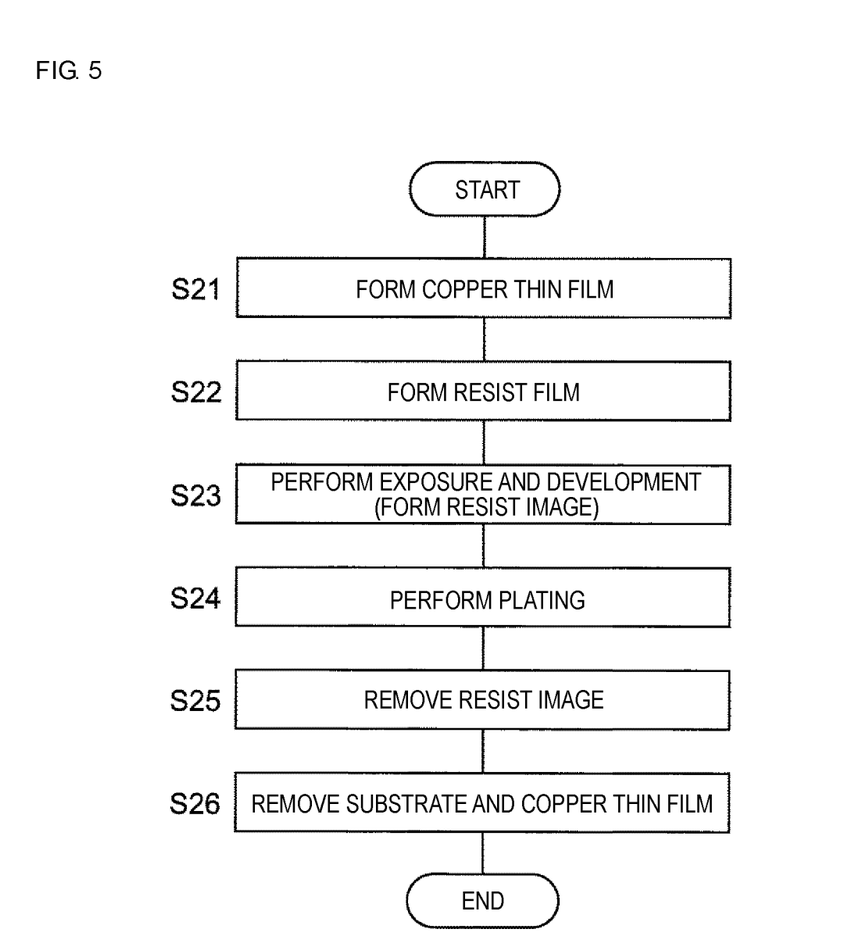
FIG. 5 is a flowchart of a method for manufacturing a filter according to an embodiment of the present invention.

Subsequently, an example of a method for manufacturing the filter 1 according to the present first embodiment is described. FIG. 5 illustrates a flowchart of a method for manufacturing the filter 1, and FIG. 6(A) to FIG. 6(F) illustrate sections of the filter 1 in manufacturing processes in the manufacturing method.

Figure 6A:
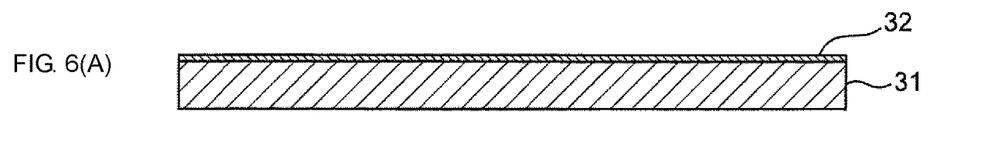
FIGS. 6(A) to 6(F) are schematic sectional views of processes in the method for manufacturing a filter illustrated in FIG. 5.

In step S21 (forming of a copper thin film) in FIG. 5, a metal film is formed. As illustrated in FIG. 6(A), a metal film is formed on a substrate 31 made of, for example, silicon. Copper is used as an example of a metal forming the metal film, and a copper thin film 32 is formed on the substrate 31. The copper thin film 32 can be formed by, for example, vapor deposition or sputtering. The surface film has higher quality when formed by sputtering than when formed by vapor deposition. This copper thin film 32 is used as a feeder electrode during plating, described below. An intermediate layer (for example, Ti film) may be formed to secure adhesion between the substrate 31 and the copper thin film 32.

Figure 6B:
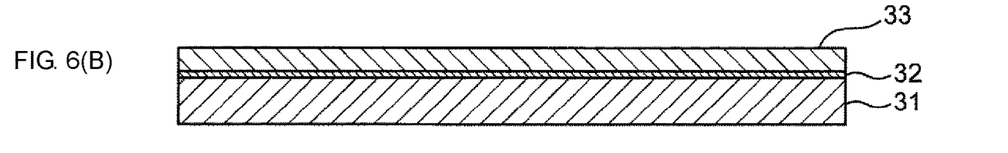

As illustrated in FIG. 6(B), subsequently, a resist film 33 is formed on the copper thin film 32 (step S22, forming of a resist film). Specifically, a resist is applied to the copper thin film 32 by, for example, spin coating, and dried to form a resist film 33. The resist film 33 has a thickness of, for example, approximately 2 µm.

Figure 6C:
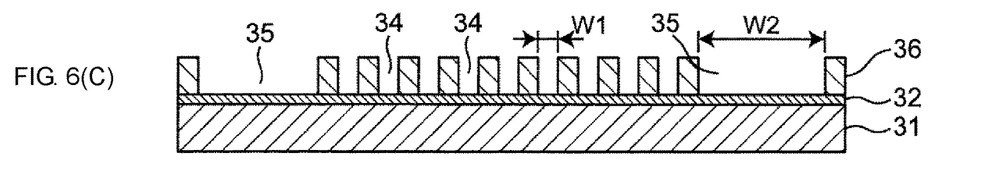

Subsequently, as illustrated in FIG. 6(C), the resist film 33 is exposed to light and subjected to development to form a resist image 36 including groove portions 34 and 35, by removing portions corresponding to the metallic porous film 10 from the resist film 33 (step S23, exposure and development (forming of a resist image)). The groove portions 34 are groove portions formed in the filtering portion R1 of the metallic porous film 10, and the groove portion 35 is a groove portion formed in the frame portion R2. The opening width W1 of the groove portions 34 corresponds to the distance between the adjacent through holes 11 in the metallic porous film 10, and the opening width W2 of the groove portion 35 corresponds to the width of the frame portion R2. Specifically, the opening width W1 of the groove portions 34 is smaller than the opening width W2 of the groove portion 35. The copper thin film 32 is exposed at the bottom of the groove portions 34 and 35.

Figure 6D:
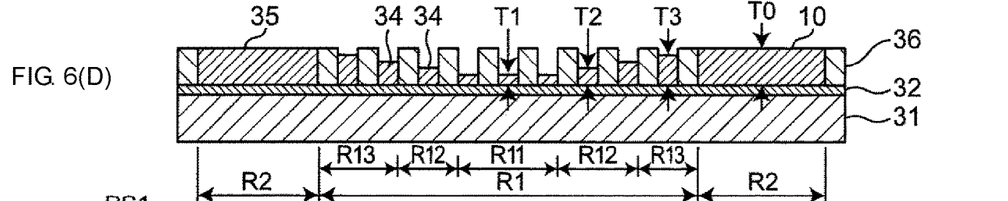

Subsequently, as illustrated in FIG. 6(D), in the resist image 36, a metallic porous film 10 is formed in the groove portions 34 and 35 by depositing metal, as a main material, in the groove portions 34 and 35 (step S24, plating). The metallic porous film 10 is formed by electroplating using, for example, the copper thin film 32 as a feeder electrode. Nickel is an example of a deposited metal.

As described above, in the resist image 36, the opening width W1 of the groove portions 34 is smaller than the opening width W2 of the groove portion 35. In the resist image 36, the groove portions 34 are densely formed in the center portion, and the groove portion 35 is annularly formed to surround these groove portions 34. When the resist image 36 in this state is plated, a plating solution smoothly enters the groove portion 35 having a large opening width, whereas the plating solution enters with difficulty the groove portions 34 having a small opening width. Even within the area where the groove portions 34 are formed, the plating solution enters the groove portions 34 in a portion corresponding to the central area R11 of the filtering portion R1, in which the groove portions 34 are surrounded by other groove portions 34, with greater difficulty than the portion corresponding to the peripheral area R13 located closer to the frame portion R2. This is probably because protrusions of the resist image 36 defining the groove portions 34 are densely arranged to hinder the plating solution from entering the groove portions 34. As the plating rate is increased further, the smoothness of the plating solution in entering the groove portions varies more significantly.

After plating in this manner, the plating solution that has entered the groove portions 34 and 35 forms a precipitate, and forms a film with the precipitated metal having a film thickness proportional to the amount of the plating solution that has entered the groove portions 34 and 35. As illustrated in FIG. 6(D), the film thickness T0 of the metallic porous film 10 formed in the groove portion 35 is the maximum. In the groove portions 34, the film thickness T3 at the boundary (points of intersection P3) between the peripheral area R13 and the intermediate area R12, the film thickness T2 at the boundary (points of intersection P2) between the intermediate area R12 and the central area R11, and the film thickness T1 at the center P1 of the central area R11 descend in this order.

Figure 6E:
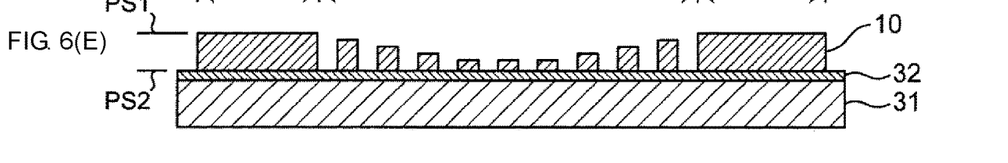

Subsequently, as illustrated in FIG. 6(E), the workpiece is immersed in a solvent (for example, acetone) to dissolve the resist image 36 to detach the metallic porous film 10 from the copper thin film 32 (step S25, removal of a resist image).

Figure 6F:
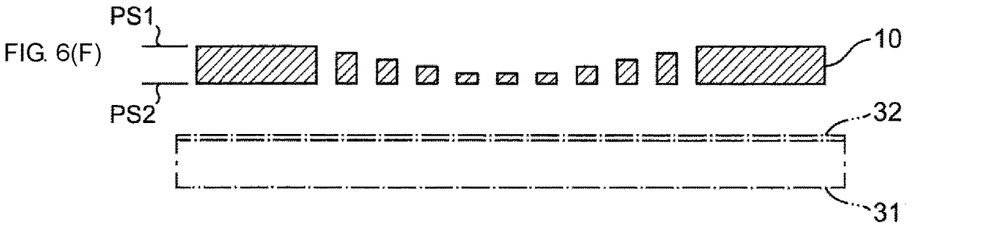

Subsequently, as illustrated in FIG. 6(F), the copper thin film 32 and the substrate 31 are removed, (step S26, removal of the substrate and the copper thin film). Specifically, the copper thin film 32 is removed by etching using an etchant to detach the metallic porous film 10 from the substrate 31.

This procedure forms the metallic porous film 10 including a filtering portion R1 including the multiple through holes 11, and a frame portion R2 around the filtering portion R1. The first main surface PS1 forms a concave surface with its film thickness descending in order of the film thickness T0 of the frame portion R2 of the metallic porous film 10, the film thickness T3 at the points of intersection P3 of the filtering portion R1, the film thickness T2 at the points of intersection P2, and the film thickness T1 at the center P1. On the other hand, the second main surface PS2 of the metallic porous film 10, which has been in contact with the copper thin film 32, is a flat surface. This manufacturing method manufactures a filter 1 including the metallic porous film 10 having a first main surface formed as a concave surface and a second main surface formed as a flat surface.

Figure 7:
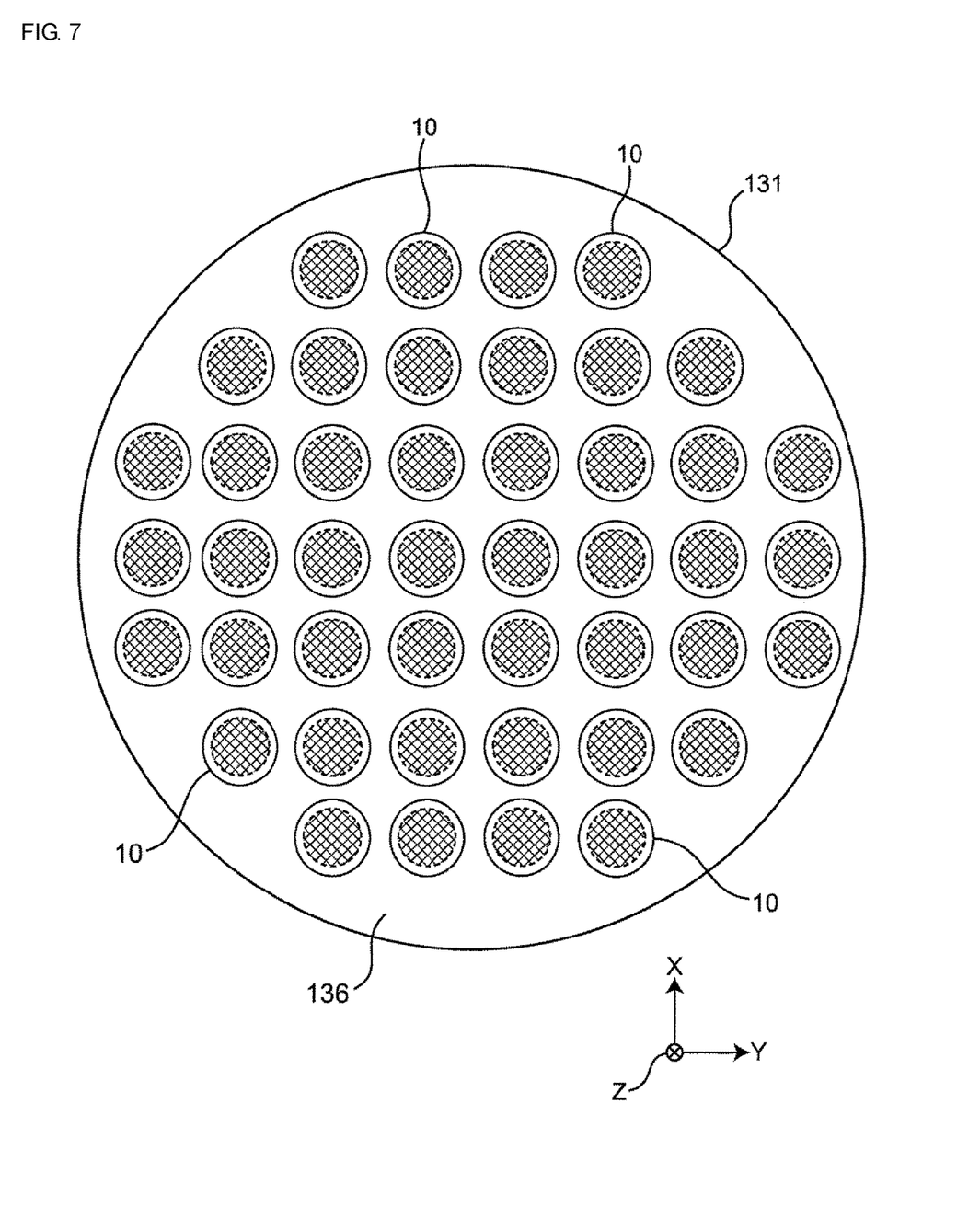
FIG. 7 is a plan view of a resist image for concurrently manufacturing multiple metallic porous films with the method for manufacturing a filter according to a modification example of the present invention.

The method for manufacturing the filter 1 is not limited to the case of manufacturing a single metallic porous film 10 from a single substrate 31. For example, as illustrated in FIG. 7, a resist image 136, which is a group of resist images 36 corresponding to multiple metallic porous films 10, may be formed on a single substrate 131 to concurrently manufacture the multiple metallic porous films 10.

In the filter 1 according to the present first embodiment, the first main surface PS1 in the filtering portion R1 of the metallic porous film 10 is formed into a concave surface so that the film thickness T1 at the center P1 of the filtering portion R1 is smaller than the film thicknesses T2 and T3 located at the positions closer to the frame portion R2 than the center P1. This structure facilitates formation of a fluid puddle on the concave surface with the effect of the surface tension of the fluid when cells are captured on the first main surface PS1 having the concave surface. For example, handling the captured cells while being left on the concave surface in the culture solution serving as a liquid pool enables a process such as an analysis while the cells are prevented from being dried. Thus, the handleability of the cells captured by the metallic porous film 10 can be improved.

In the filtering portion R1, the film thickness of the metallic porous film 10 increases continuously or stepwise from the center P1 of the filtering portion R1 toward the frame portion R1 to form a smooth concave surface on the metallic porous film 10. This structure enables formation of a fluid puddle on the concave surface with the effect of the surface tension, and further improves the handleability of cells captured by the metallic porous film 10.

The second main surface PS2 of the metallic porous film is a flat surface, and the first main surface PS1 is a concave surface. Thus, for example, to use a fluid puddle formed using the concave surface, cells may be captured on the first main surface PS1, which forms a concave surface. On the other hand, to facilitate removal of the fluid without forming a fluid puddle, cells can be captured on the second main surface PS2, which is a flat surface. The first main surface PS1 and the second main surface PS2 are thus differently used for difference purposes to improve the handleability of the cell-capturing filter.

In the metallic porous film 10, the width of the frame portion R2 is greater than the distance between adjacent through holes 11 in the filtering portion R1. Making the width of the frame portion R2 different from the distance between adjacent through holes 11 enables varying the smoothness with which the plating solution enters the groove portions 34 and 35 during, for example, plating using the resist image 36. This structure can vary the film thickness so that the filtering portion R1 has a concave surface. This structure can thus provide the filter 1 that can improve the handleability of cells captured by the metallic porous film 10.

The above embodiment describes the case, as an example, where a concave surface is formed to have a film thickness that increases continuously or stepwise in the filtering portion R1 of the metallic porous film 10 from the center P1 of the filtering portion R1 toward the frame portion R2. However, the present invention is not limited to the above case. For example, a portion having a film thickness increasing from the frame portion R2 toward the center P1 of the filtering portion R1 may be included partially in the filtering portion R1. Even such a structure can have the effects of the present invention as long as the average film thickness in the central area R11 in the filtering portion R1 as a whole is smaller than the average film thickness in the peripheral area R13.

An example of a method for manufacturing a filter according to the present invention is described below.

EXAMPLE

In this example, a filter 1 was fabricated by performing steps S21 to S26 in FIG. 5.

Firstly, in step S21, a copper thin film was formed on the upper surface of a silicon substrate using a sputtering device. The copper thin film was formed by using an argon gas as a sputtering gas, at a degree of vacuum in the sputtering device of $5.0 \times 10^{-4}$ Pa, and with an application of an electric power of DC 500 W. Sputtering was performed for 27 minutes to form the copper thin film.

Subsequently, in step 22, a resist film having a predetermined film thickness was formed on the copper thin film using a spin coater. Specifically, a resist agent was applied onto the copper thin film, and the solvent was left in an atmosphere of nitrogen at 130° C. to volatilize and then cooled to form a resist film. The resist film having a film thickness of 2 μm was formed with the spin coater at the number of revolutions of 1130 rpm using a novolak resin and an organic solvent for the resist agent.

Subsequently, in step S23, the resist film was exposed to light and subjected to development to form a resist image in which a groove portion corresponding to a metallic porous film is formed on the resist film. The resist film was exposed to light by being irradiated with a light beam with an energy density of 2500 J/m$^2$ containing a wavelength of 365 nm for 0.25 seconds. Thereafter, the portion of the resist film exposed to light was brought into contact with an alkaline solution to be removed to form a groove portion. In the resist image, the groove portions in a portion corresponding to the frame portion of the metallic porous film have an opening width of 0.8 mm, and the groove portion in a portion corresponding to the filtering portion has an opening width of 0.8 μm.

Subsequently, in step S24, a metallic porous film formed of a plated film containing nickel as a main component was formed by electroplating in the groove portions of the resist image using the previously formed copper thin film as a feeder electrode. Firstly, as preprocessing, the substrate having a copper thin film and a resist image formed thereon was immersed in a dilute sulfuric acid for 60 seconds to activate the surface of the copper thin film exposed at the bottom of the groove portion of the resist image. Thereafter, while being shaken in a sulfamic acid nickel plating solution (liquid temperature of 55° C., and pH 4.0), the substrate was subjected to electroplating while receiving a voltage using the copper thin film as a feeder electrode. The speed of plating was 0.5 μm/min.

Thereafter, in step S25, the substrate was immersed in the solvent to dissolve the resist image and to detach the resist image from the copper thin film. In an acetone solution used as a solvent, the substrate received ultrasonic waves for 15 minutes to accelerate dissolution and separation of the resist image.

Subsequently, in step S26, the copper thin film and the substrate were removed. Specifically, the copper thin film was etched by being immersed for 48 hours in the environment of 25° C. in a solution, serving as an etchant, formed by mixing a 60% hydrogen peroxide solution, acetic acid, and pure water at a volume ratio of 1:1:20. Thus, the copper thin film and the substrate were removed to complete a filter including a metallic porous film according to the example.

In measurements of the metallic porous film according to the example, the contour of the frame portion R2 (that is, the diameter of the metallic porous film) was 8 mm, the diameter of the filtering portion R1 was 6 mm, the film thickness of the center P1 of the filtering portion R1 was 0.7 μm, and the film thickness at the boundary (points of intersection P3) between the peripheral area R13 and the intermediate area R12 was 1.2 μm.

Any of the above-described embodiments may be combined appropriately to exert their effects.

INDUSTRIAL APPLICABILITY

In the present invention, at least one of the first main surface and the second main surface in the filtering portion of the filter partially includes a concave surface. When cells are to be captured on the concave surface, the concave surface is more likely to allow a fluid puddle formed thereon with the effect of the surface tension of a fluid. This structure can thus prevent captured cells from being dried, and thus improves the handleability of cells captured by the metallic porous film and the handleability of the metallic porous film. The present invention is thus applicable to various different technical fields in which such a filter is usable, for example, the field of chemical analysis, drug design or drug development, clinical examination, public health management, or environmental measurement.

REFERENCE SIGNS LIST 1 filter
10 metallic porous film
11 through hole
31 substrate
32 copper thin film
33 resist film
34, 35 groove portion
36 resist image
PS1 first main surface
PS2 second main surface
R1 filtering portion
R2 frame portion
R11 central area
R12 intermediate area
R13 peripheral area
C1, C2 imaginary circle
D1, D2, D3 radius
L imaginary straight line
P1 center
P2, P3 point of intersection
T0, T1, T2, T3 film thickness
W1, W2 opening width

The invention claimed is:

1. A cell-capturing filter that filters out cells, the cell-capturing filter comprising:
   a metallic porous film including a plurality of through holes that extend through a first main surface and a second main surface which are opposite to each other;
   wherein the metallic porous film includes
      a filtering portion that includes the plurality of through holes, and
      a frame portion surrounding an outer periphery of the filtering portion, and
   wherein a first film thickness of the metallic porous film at a center of the filtering portion is smaller than a second film thickness of the metallic porous film at a portion of the metallic porous film closer to the frame portion than the center of the filtering portion such that at least one of the first main surface and the second main surface has a concave surface in the filtering portion, and the concave surface is configured to allow a fluid puddle to be formed thereon so that captured cells are prevented from being dried.

2. The cell-capturing filter according to claim 1, wherein, in the filtering portion, the film thickness of the metallic porous film increases continuously or stepwise from the center of the filtering portion toward the frame portion.

3. The cell-capturing filter according to claim 1, wherein the second main surface of the metallic porous film is a flat surface, and the first main surface at the filtering portion is the concave surface.

4. The cell-capturing filter according to claim 1, wherein, in a direction parallel to the second main surface of the metallic porous film, the frame portion has a width greater than a distance between adjacent through holes of the plurality of through holes in the filtering portion.

5. The cell-capturing filter according to claim 1, wherein the metallic porous film contains gold, silver, copper, nickel, stainless steel, palladium, titanium, or an alloy thereof as a main component.

6. The cell-capturing filter according to claim 1, wherein the plurality of through holes are arranged in a matrix at regular intervals in the filtering portion.

7. The cell-capturing filter according to claim 1, wherein the plurality of through holes have a square shape when viewed from the first main surface.

8. The cell-capturing filter according to claim 1, wherein the first film thickness is 0.8 µm.

9. A cell-capturing filter that filters out cells, the cell-capturing filter comprising:
a substrate; and
a plurality of metallic porous films in the substrate, wherein each of the plurality of metallic porous films include:
a plurality of through holes that extend through a first main surface and a second main surface which are opposite to each other,
a filtering portion that includes the plurality of through holes, and
a frame portion surrounding an outer periphery of the filtering portion, and
wherein a first film thickness of each of the plurality of metallic porous films at a center of the filtering portion thereof is smaller than a second film thickness at a portion of each of the plurality of metallic porous films closer to the frame portion than the center of the filtering portion such that at least one of the first main surface and the second main surface has a concave surface in the filtering portion, and the concave surface is configured to allow a fluid puddle to be formed thereon so that captured cells are prevented from being dried.

10. The cell-capturing filter according to claim 9, wherein, in the filtering portion of each of the plurality of metallic porous films, the film thickness increases continuously or stepwise from the center of the filtering portion toward the frame portion.

11. The cell-capturing filter according to claim 9, wherein the second main surface of each of the plurality of metallic porous films is a flat surface, and the first main surface at the filtering portion is the concave surface.

12. The cell-capturing filter according to claim 9, wherein, in a direction parallel to the second main surface of each of the plurality of metallic porous films, the frame portion has a width greater than a distance between adjacent through holes of the plurality of through holes in the filtering portion.

13. The cell-capturing filter according to claim 9, wherein each of the plurality of metallic porous films contains gold, silver, copper, nickel, stainless steel, palladium, titanium, or an alloy thereof as a main component.

14. The cell-capturing filter according to claim 9, wherein the plurality of through holes of each of the plurality of metallic porous films are arranged in a matrix at regular intervals in the filtering portion thereof.

15. The cell-capturing filter according to claim 9, wherein the plurality of through holes of each of the plurality of metallic porous films have a square shape when viewed from the first main surface.

16. The cell-capturing filter according to claim 9, wherein the first film thickness is 0.8 µm.

17. The cell-capturing filter according to claim 1, wherein
the metallic porous film at the center of the filtering portion is a central area having the first film thickness,
the portion of the metallic porous film closer to the frame portion than the center of the filtering portion is an intermediate area having the second film thickness, and
the metallic porous film has a peripheral area closer to the frame portion than the intermediate area and having a third film thickness, and where the second film thickness is smaller than the third film thickness.

* * * * *